US011512037B2

(12) United States Patent
Tabuchi et al.

(10) Patent No.: US 11,512,037 B2
(45) Date of Patent: Nov. 29, 2022

(54) PROCESS FOR PRODUCING DIMETHYL 2,3,5,6-TETRACHLORO-1,4-BENZENEDICARBOXYLATE

(71) Applicant: SDS BIOTECH K.K., Tokyo (JP)

(72) Inventors: Toshihiko Tabuchi, Tokyo (JP); Masaaki Sakai, Tokyo (JP); Teruhiko Ishii, Tsukuba (JP)

(73) Assignee: SDS BIOTECH K.K., Tokyo (JP)

(*) Notice: Subject to any disclaimer, the term of this patent is extended or adjusted under 35 U.S.C. 154(b) by 0 days.

(21) Appl. No.: 17/635,653

(22) PCT Filed: Jan. 25, 2021

(86) PCT No.: PCT/JP2021/002403
§ 371 (c)(1),
(2) Date: Feb. 15, 2022

(87) PCT Pub. No.: WO2022/085211
PCT Pub. Date: Apr. 28, 2022

(65) Prior Publication Data
US 2022/0267244 A1  Aug. 25, 2022

(30) Foreign Application Priority Data
Oct. 20, 2020  (JP) .............................. JP2020-175862

(51) Int. Cl.
*C07C 67/02* (2006.01)
*C07C 67/52* (2006.01)
*C07C 51/08* (2006.01)
*C07C 63/26* (2006.01)
*C07C 69/76* (2006.01)
*C07C 67/11* (2006.01)

(52) U.S. Cl.
CPC .............. *C07C 67/02* (2013.01); *C07C 51/08* (2013.01); *C07C 63/26* (2013.01); *C07C 67/11* (2013.01); *C07C 67/52* (2013.01); *C07C 69/76* (2013.01)

(58) Field of Classification Search
CPC ......... C07C 67/02; C07C 67/11; C07C 67/52; C07C 51/08; C07C 63/14; C07C 63/26; C07C 69/76
See application file for complete search history.

(56) References Cited

U.S. PATENT DOCUMENTS

| 3,052,712 A | 9/1962 | Zinn |
| 3,689,526 A | 9/1972 | Hanna |
| 3,689,527 A | 9/1972 | Hanna |
| 3,833,652 A | 9/1974 | Knobloch |
| 3,873,613 A | 3/1975 | Knobloch et al. |
| 4,808,345 A | 2/1989 | Pontoglio et al. |
| 6,452,046 B2* | 9/2002 | Matsushita ............. C07C 51/06 504/144 |
| 2001/0025121 A1 | 9/2001 | Matsushita et al. |
| 2019/0055323 A1 | 2/2019 | Kakubari et al. |

FOREIGN PATENT DOCUMENTS

| CN | 106986767 A | * | 7/2017 | ............. C07C 67/11 |
| CN | 106986767 A |  | 7/2017 | |
| DE | 1078563 B |  | 3/1960 | |
| JP | 48-13339 B1 |  | 4/1973 | |
| JP | 51-138641 A |  | 11/1976 | |
| JP | 58-157727 A |  | 9/1983 | |
| JP | 60-16952 A |  | 1/1985 | |
| JP | 10-251119 A |  | 9/1998 | |
| JP | 10-251301 A |  | 9/1998 | |
| JP | 10-251446 A |  | 9/1998 | |
| JP | 11-140793 A |  | 5/1999 | |
| JP | 2002-194001 A |  | 7/2002 | |
| JP | 2007-191558 A |  | 8/2007 | |
| JP | 2008-222859 A |  | 9/2008 | |
| JP | 2015-149929 A |  | 8/2015 | |
| JP | 2015-149930 A |  | 8/2015 | |
| JP | 2017-149901 A |  | 8/2017 | |
| JP | 6337225 B1 |  | 6/2018 | |
| JP | 6351821 B1 |  | 7/2018 | |
| JP | 2018-164443 A |  | 10/2018 | |
| JP | 6417490 B1 |  | 11/2018 | |
| JP | 6442106 B1 |  | 12/2018 | |
| JP | 6505900 B1 |  | 4/2019 | |
| JP | 6505901 B1 |  | 4/2019 | |
| SU | 352882 A1 |  | 9/1972 | |
| WO | 2014/087767 A1 |  | 6/2014 | |
| WO | 2014/088072 A1 |  | 6/2014 | |

OTHER PUBLICATIONS

Popova et a., Preparation of dimethyl ether of tetrachlorotherephthalic acid, Zhurnal Priklandnoi Khimii, 51(6), 1422-1423 (Year: 1978).*
Guseynov et al., Chlorination of Terephthalic Acid. Vop Neftekhim. 1971;3:49-51.
Popova et al.. Preparation of Dimethyl Ether of Tetrachlorotherephthalic Acid. Zhurnal Prikladnoi Khimii. 1978;51(6):1422-1423.
Sheng et al., Synthesis and Characterization of Novel Polychloro-substituted Poly (aryl ether ketone sulfone) Random Copolymers. Chinese Journal of Applied Chemistry. Apr. 2005;22(4):387-390.
Sheng et al., Synthesis of Soluble Polychloro Substituted Poly (Aryletherketoneketone). Acta Polymerica Sinica. 2004 Oct. 5:773-775.
Yakobson et al., Aromatic Fluorine Derivatives. XIV. Tetrafluoroterephthalic Acid. Zhurnal Obschchei Khimii. 1964;34(9):2953-2958.
International Search Report and Written Opinion for Application No. PCT/JP2019/019670, dated Jul. 2, 2019, 41 pages.

(Continued)

*Primary Examiner* — Yate' K Cutliff
(74) *Attorney, Agent, or Firm* — McCarter & English, LLP; Steven G. Davis; Wei Song

(57) ABSTRACT

The present invention provides a process for producing a compound represented by formula (I), comprising the steps of (a) reacting a compound represented by formula (II) with dimethyl sulfate in the presence of an alkali carbonate in a aqueous ketone solvent to obtain the compound represented by formula (I) as a crystalline material, and (b) washing the crystalline material with heated water at 30 to 100° C. and then further washing with an organic solvent at 30 to 80° C.

25 Claims, No Drawings

(56) References Cited

OTHER PUBLICATIONS

International Search Report and Written Opinion for Application No. PCT/JP2021/002403, dated Feb. 16, 2021, 13 pages.
Sheng et al., Synthesis of Soluble Polychloro Substituted Poly (Aryletherketoneketone). Acta Polymerica Sinica. Oct. 5, 2004:773-775.

* cited by examiner

PROCESS FOR PRODUCING DIMETHYL 2,3,5,6-TETRACHLORO-1,4-BENZENEDICARBOXYLATE

CROSS-REFERENCE TO RELATED APPLICATIONS

This application is a U.S. national stage application, filed under 35 U.S.C. § 371(c), of International Patent Application No. PCT/JP2021/002403, filed on Jan. 25, 2021, which claims priority to Japanese Patent Application No. 2020-175862, filed on Oct. 20, 2020.

TECHNICAL FIELD

The present invention relates to a process for producing dimethyl 2,3,5,6-tetrachloro-1,4-benzenedicarboxylate.

BACKGROUND ART

As represented in reaction formula 1 below, dimethyl 2,3,5,6-tetrachloro-1,4-benzenedicarboxylate (formula (I) below) has been produced by a process of methyl esterifying 2,3,5,6-tetrachloro-1,4-benzenedicarboxylic acid (formula (II) below) with methanol and sulfur trioxide/sulfuric acid/chlorosulfate (PTL 1), a process of mono-methyl esterifying 2,3,5,6-tetrachloro-1,4-benzenedicarboxylic acid with dimethyl sulfate in a potassium hydroxide aqueous solution and then further esterifying an unreacted carboxyl group with methanol/a strong acid (PTL 2), or a process of methyl esterifying 2,3,5,6-tetrachloro-1,4-benzenedicarboxylic acid in a non-aqueous system in acetone in the presence of dimethyl sulfate and sodium carbonate (NPL 1).

[Chemical Formula 1]

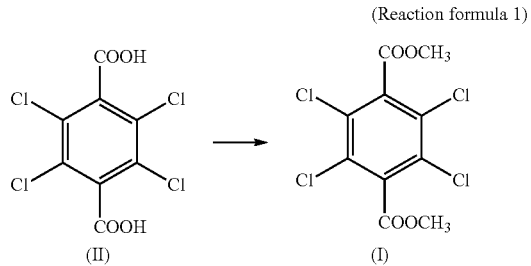

(Reaction formula 1)

Moreover, as represented in reaction formula 2 below, dimethyl 2,3,5,6-tetrachloro-1,4-benzenedicarboxylate (formula (I) below) is produced also by a method of methyl esterifying 2,3,5,6-tetrachloro-1,4-benzenedicarbonyl chloride (formula (IV) below) with methanol and an alkali (PTL 3).

[Chemical Formula 2]

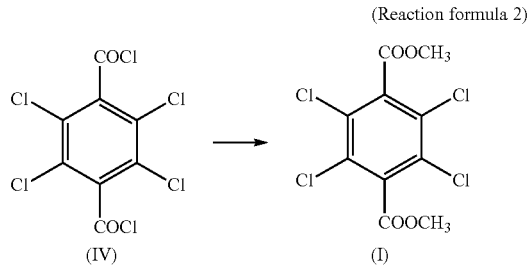

(Reaction formula 2)

In the process for producing dimethyl 2,3,5,6-tetrachloro-1,4-benzenedicarboxylate represented by the above reaction formula 1, 2,3,5,6-tetrachloro-1,4-benzenedicarboxylic acid obtained by chlorination on the aromatic ring of terephthalic acid is used as a raw material. A process for producing 2,3,5,6-tetrachloro-1,4-benzenedicarboxylic acid that is the raw material is disclosed in PTLs 4 to 6 and NPLs 2 and 3 that are prior art.

Moreover, PTL 7 describes, as another process for producing 2,3,5,6-tetrachloro-1,4-benzenedicarboxylic acid, a process for converting a CN group of 2,3,5,6-tetrachloro-1,4-benzenedicarbonitrile to an amide group to obtain 2,3,5,6-tetrachloro-1,4-benzenedicarboxamide, and then producing 2,3,5,6-tetrachloroterephthalic acid by using fuming sulfuric acid, etc.

On the other hand, in the process for producing dimethyl 2,3,5,6-tetrachloro-1,4-benzenedicarboxylate represented by reaction formula 2, 2,3,5,6-tetrachloroterephthalic acid dichloride is used as a raw material, and this raw material is obtained by chlorination on the aromatic ring of terephthalic acid dichloride (PTLs 8 to 13, NPLs 4 and 5).

CITATION LIST

Patent Literature

PTL 1: U.S. Pat. No. 3,689,526 A
PTL 2: U.S. Pat. No. 3,689,527 A
PTL 3: JP S60-16952 A
PTL 4: U.S. Pat. No. 3,873,613 A
PTL 5: SU 352882 A1
PTL 6: DE 1078563 B
PTL 7: US 2001/0025121 A1
PTL 8: JP S48-013339 A
PTL 9: JP S51-138641 A
PTL 10: JP S58-157727 A
PTL 11: U.S. Pat. No. 3,052,712 A
PTL 12: U.S. Pat. No. 3,833,652 A
PTL 13: U.S. Pat. No. 4,808,345 A

Non Patent Literature

NPL 1: Zhurnal Prikladnoi Khimii, (1978), 51(6), 1422-1423
NPL 2: Vop. Neftekhim, (1971), No. 3, 49-51
NPL 3: Zhurnal Obshchei Khimii, (1964), 34(9), 2953-2958
NPL 4: Gaofenzi Xuebao, (2004), (5), 773-775
NPL 5: Yingyong Huaxue, (2005), 22(4), 317-390

SUMMARY OF INVENTION

Technical Problem

Regarding the process for producing the aforementioned reaction formula 1, the production processes described in PTLs 1 and 2 are complicated as being two-step reactions. Moreover, the production process described in NPL 1 has a problem in that due to the remaining unreacted raw materials, the reaction cannot be completed.

According to the process for producing 2,3,5,6-tetrachloro-1,4-benzenedicarboxylic acid described in PTLs 4 to 6 and NPLs 2 and 3 described above, hexachlorobenzene that is an unfavorable by-product is produced in a considerable amount, and the obtained 2,3,5,6-tetrachloro-1,4-benzenedicarboxylic acid contains a large amount of hexachlorobenzene. When 2,3,5,6-tetrachloro-1,4-benzenedicarboxylic acid containing a large amount of hexachlorobenzene thus obtained is used as a raw material to produce dimethyl 2,3,5,6-tetrachloro-1,4-benzenedicarboxylate, hexachlorobenzene is present also in the obtained dimethyl 2,3,5,6-tetrachloro-1,4-benzenedicarboxylate at an unacceptable concentration.

The process for producing 2,3,5,6-tetrachloro-1,4-benzenedicarboxylic acid described in PTL 7 described above can inhibit the mass production of by-products, such as hexachlorobenzene, but it is not only complicated due to the two-step reaction process, but also dangerous in handling the raw materials because fuming sulfuric acid, etc., is used.

In the chlorination on the aromatic ring of terephthalic acid dichloride described in PTLs 8 to 13 and NPLs 4 and 5 described above, it is difficult to control the generation of hexachlorobenzene, and the obtained 2,3,5,6-tetrachloroterephthalic acid dichloride contains a large amount of hexachlorobenzene. When producing dimethyl 2,3,5,6-tetrachloro-1,4-benzenedicarboxylate by using 2,3,5,6-tetrachloroterephthalic acid dichloride containing a large amount of hexachlorobenzene, hexachlorobenzene is present at an unacceptable concentration also in the obtained dimethyl 2,3,5,6-tetrachloro-1,4-benzenedicarboxylate.

An object of the present invention is to provide an industrial process capable of reducing the content of a by-product poisonous to the environment, such as hexachlorobenzene and pentachlorobenzene, compared with a conventional process to thereby enable the efficient production for producing dimethyl 2,3,5,6-tetrachloro-1,4-benzenedicarboxylate useful as agricultural and horticultural herbicides.

Solution to Problem

As a result of intensive experimentation to solve the above problems, the present inventors have realized a large reduction of the contents of by-products, hexachlorobenzene and pentachlorobenzene, by employing specific conditions for washing a crystalline material of dimethyl 2,3,5,6-tetrachloro-1,4-benzenedicarboxylate, and thus have completed the present invention.

Specific aspects of the present invention are as follows.

[1] A process for producing a compound represented by formula (I):

[Chemical Formula 3]

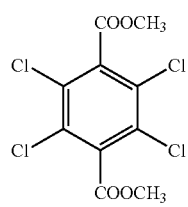

(I)

the process comprising the steps of
(a) reacting a compound represented by formula (II):

[Chemical Formula 4]

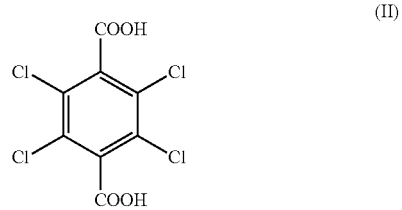

(II)

with dimethyl sulfate in the presence of an alkali carbonate in a aqueous ketone solvent to obtain the compound represented by formula (I) as a crystalline material, and
(b) washing the crystalline material with heated water at 30 to 100° C. and then further washing the crystalline material with an organic solvent at 30 to 80° C. [2] The process according to [1], wherein step (b) is a step of reducing the content of a poisonous by-product contained in the crystalline material by washing the crystalline material with an organic solvent under heating.
[3] The process according to [1] or [2], wherein in step (b), a temperature of the crystalline material after washing with heated water and before washing with an organic solvent is 40 to 90° C.
[4] The process according to any one of [1] to [3], wherein a temperature of the heated water is 60 to 95° C.
[5] The process according to any one of [1] to [4], wherein the organic solvent in step (b) is an alcohol.
[6] The process according to any one of [1] to [5], wherein the organic solvent in step (b) is methanol, ethanol, isopropanol, or a mixture thereof.
[7] The process according to any one of [1] to [6], wherein the organic solvent in step (b) is methanol.
[8] The process according to any one of [5] to [7], wherein a temperature of the organic solvent is 35 to 65° C.
[9] The process according to any one of [1] to [8], further comprising, before step (a), the step of
(a') heating a compound represented by formula (III):

[Chemical Formula 5]

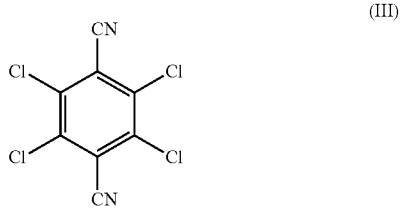

(III)

to 100 to 180° C. in the presence of an acid to obtain the compound represented by formula (II).
[10] The process according to [9], wherein the compound represented by formula (II) obtained in step (a') is used in step (a) after being washed with water.
[11] The process according to any one of [1] to [10], wherein the aqueous ketone solvent in step (a) is aqueous acetone.
[12] The process according to any one of [1] to [11], wherein a water content of the aqueous ketone solvent in step (a) is 5 to 25% by weight.

[13] The process according to any one of [1] to [12], wherein the alkali carbonate in step (a) is sodium carbonate.
[14] The process according to [2], wherein the poisonous by-product is polychlorobenzenes.
[15] The process according to [14], wherein the polychlorobenzenes are hexachlorobenzene, pentachlorobenzene, or a mixture thereof.
[16] A composition comprising a compound represented by formula (I):

[Chemical Formula 6]

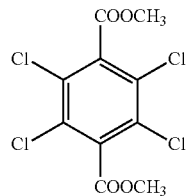

(I)

wherein a content of hexachlorobenzene contained in the composition is more than 0 ppm and 40 ppm or less, and a content of pentachlorobenzene contained in the composition is more than 0 ppm and 1000 ppm or less.
[17] The composition according to [16], which is used as a herbicide or a raw material of a herbicide.
[18] The composition according to [16] or [17], wherein the compound represented by formula (I) is in a state of a crystalline material.
[19] The composition according to any one of [16] to [18], wherein a content of the compound represented by formula (I) relative to an entire composition is 96.0 to 100% by weight.

Advantageous Effects of Invention

According to the present invention, when producing dimethyl 2,3,5,6-tetrachloro-1,4-benzenedicarboxylate useful as agricultural and horticultural herbicides, a desired product that contains less content of a poisonous by-product, such as hexachlorobenzene and pentachlorobenzene, compared with those by a conventional process, can be efficiently produced.

DESCRIPTION OF EMBODIMENTS

The process for producing the compound represented by formula (I) of the present invention will be described in more detail below. However, the present invention is not limited to the following description.

The present invention is a process for producing a compound represented by the above formula (I), comprising the steps of (a) reacting a compound represented by the above formula (II) with dimethyl sulfate in the presence of an alkali carbonate in a aqueous ketone solvent to obtain the compound represented by formula (I) as a crystalline material, and (b) washing the crystalline material with heated water at 30 to 100° C. and then further washing with an organic solvent at 30 to 80° C.

(Step (a))

The compound (2,3,5,6-tetrachloro-1,4-benzenedicarboxylic acid) represented by formula (II) used in step (a) can be produced by a publicly known production process, for example, by step (a') described later.

The aqueous ketone solvent used in step (a) is not particularly limited, but is preferably aqueous acetone, aqueous 2-butanone, aqueous 3-pentanone, or a mixture thereof, and is particularly preferably aqueous acetone among them from the viewpoints of the affinity with water and the cost.

The water content of the aqueous ketone solvent is not particularly limited, but is preferably 5 to 25% by weight, more preferably 10 to 20% by weight, and most preferably 15 to 20% by weight. As used herein, the water content of the aqueous ketone solvent refers to a content measured by a volumetric titration method based on the conditions described in JIS K0068 by using a Karl Fischer electric titrator. When the water content of the aqueous ketone solvent is within the above numerical range, the effect whereby the reaction is completed and the yield of the target product is stabilized, is exhibited.

The water content of the aqueous ketone solvent can be adjusted by adding water to the reaction mixture in step (a).

The amount of the aqueous ketone solvent added for use in step (a) is preferably 1.0 to 5.0 L, more preferably 1.0 to 3.0 L, and most preferably 1.2 to 2.0 L, based on 1 kg of the compound represented by formula (II).

The alkali carbonate used in step (a) is not particularly limited, but is preferably sodium carbonate, potassium carbonate, cesium carbonate, or a mixture thereof, and is particularly preferably sodium carbonate among them from the viewpoints of the cost and the yield.

The amount of the alkali carbonate added for use in step (a) is preferably 1.0 to 5.0 equivalents, more preferably 1.0 to 3.0 equivalents, and most preferably 1.2 to 2.0 equivalents, relative to the compound represented by formula (II).

The amount of dimethyl sulfate added for use in step (a) is preferably 1.5 to 4.0 equivalents, more preferably 1.7 to 3.0 equivalents, and most preferably 2.0 to 2.5 equivalents, relative to the compound represented by formula (II).

The reaction temperature in step (a) is not particularly limited, but a temperature at which the solvent is refluxed is preferred, and specifically the reaction temperature is preferably 40 to 100° C., more preferably 50 to 80° C., and most preferably 55 to 65° C.

The reaction time in step (a) is not particularly limited, but is preferably 2 to 10 hours, more preferably 4 to 8 hours, and most preferably 4 to 6 hours.

From the reaction mixture containing the crystalline material of the compound represented by formula (I) which is obtained in step (a), the aqueous ketone solvent is preferably distilled off. The conditions for distilling off the aqueous ketone solvent are not particularly limited, but the pressure is preferably adjusted to normal pressure or reduced pressure, and regarding the temperature, heating is preferred, in which hot water or steam can be used.

The crystalline material of the compound represented by formula (I) can be precipitated by adding heated water at 40 to 50° C. to the reaction mixture containing the crystalline material of the compound represented by formula (I) which is obtained in step (a) and cooling it. The crystalline material that has been precipitated in this way can be collected by filtration.

The crystalline material of the compound represented by formula (I) which is obtained in step (a) can be collected by filtration. The filtration method is not particularly limited, but vacuum filtration, pressure filtration or centrifugal filtration can be employed. The filtration conditions are not particularly limited, but decompression or pressurization conditions can be adopted.

(Step (b))

The temperature of the heated water used in step (b) is 30 to 100° C., preferably 60 to 95° C., and more preferably 85 to 90° C. When the temperature of the heated water is within the above numerical range, the crystalline material of the compound represented by formula (I) can be heated, and the crystalline material in a state of being heated can be subjected to the following washing processing with an organic solvent.

The amount of heated water used in step (b) is preferably 0.5 to 3.0 L, more preferably 1.0 to 2.5 L, and most preferably 1.2 to 2.0 L, relative to 1 kg of the compound represented by formula (II).

In step (b), the temperature of the crystalline material of the compound represented by formula (I) after addition of heated water and before addition of an organic solvent is preferably 40 to 90° C., more preferably 50 to 80° C., and most preferably 60 to 75° C. When the temperature of the crystalline material is within the above numerical range, the crystalline material in a state of being heated can be subjected to the next processing with an organic solvent.

The temperature of the organic solvent used in step (b) is 30 to 80° C., preferably 35 to 65° C., and more preferably 40 to 50° C. When the temperature of the organic solvent is within the above numerical range, the content of a poisonous by-product contained in the crystalline material of the compound represented by formula (I) can be efficiently reduced.

The organic solvent used in step (b) is not particularly limited, but an alcohol is effective, and the organic solvent is preferably methanol, ethanol, or isopropanol, and is particularly preferably methanol among them from the viewpoints of the cost and the washing efficiency. The organic solvent used in step (b) may also be a mixture of two or more of the aforementioned methanol, ethanol, and isopropanol. The organic solvent used in step (b) may be a general-purpose product for use, and the purity of the organic solvent is preferably 100%, but may be 50 to 100%, 70 to 100%, 80 to 100%, 90 to 99.99% or 95 to 99.9%.

The amount of the organic solvent used in step (b) is preferably 0.5 to 3.0 L, more preferably 0.7 to 2.0 L, and most preferably 0.8 to 1.5 L, based on 1 kg of the compound represented by formula (II).

The washing with the organic solvent in step (b) can be performed 1 to 3 times, and is more preferably performed 2 times.

In one embodiment of the present invention, step (b) is preferably a step of reducing the content of a poisonous by-product contained in the crystalline material of the compound represented by formula (I) by washing the crystalline material of the compound represented by formula (I) with an organic solvent under heating.

In step (b) of the present invention, heating the crystalline material of the compound represented by formula (I) by washing them with heated water at 30 to 100° C., and further washing the crystalline material in the state of being heated with an organic solvent at 30 to 80° C. can be performed. Thereby, the content of a poisonous by-product contained in the crystalline material of the compound represented by formula (I) can be efficiently reduced.

In step (b), after washing with an organic solvent, the crystalline material of the compound represented by formula (I) can be centrifuged or filtered, and among these, filtration is preferably performed. The method for filtering the crystalline material of the compound represented by formula (I) is not particularly limited, but Nutsche filtration is preferably employed. The Nutsche filtration that includes a filtration step, a cake spreading/pressing step, a cake washing step, a re-slurry washing step, a drying (ventilation or vacuum) step, a cake discharging step, or a combination of one or more of these steps, can be employed for the filtration. By using the Nutsche filtration, the crystalline material can be deliquored in a state of being sufficiently impregnated with an organic solvent, which enhances the washing effect.

In step (b), after washing with an organic solvent, drying processing can be performed for the collected crystalline material of the compound represented by formula (I). The conditions of the drying processing are not particularly limited, but the temperature is preferably 20 to 150° C., more preferably 40 to 120° C., and most preferably 60 to 100° C., and the pressure is preferably 2 to 760 mmHg, more preferably 10 to 200 mmHg, and most preferably 20 to 100 mmHg.

The poisonous by-product which is to be removed from the crystalline material of the compound represented by formula (I) and the amount of which is to be reduced is not particularly limited, but is, for example, polychlorobenzenes. Such polychlorobenzenes are not particularly limited, but are, for example, hexachlorobenzene, pentachlorobenzene, or a mixture thereof The content of hexachlorobenzene contained in the crystalline material of the compound represented by formula (I) after step (b) is preferably 40 ppm or less, more preferably 10 ppm or less, and most preferably 5 ppm or less.

The content of pentachlorobenzene contained in the crystalline material of the compound represented by formula (I) after step (b) is preferably 1000 ppm or less, more preferably 500 ppm or less, and most preferably 100 ppm or less.

In the present invention, the content of hexachlorobenzene contained in the crystalline material of the compound represented by formula (I) after step (b) can be determined by an absolute calibration curve method with a gas chromatography apparatus (product name: Agilent 7890A, manufactured by Agilent Technologies) using a capillary column (product name: HP-5, column length of 30 m, column diameter of 0.53 mm ID, film thickness of 1.0 μm, manufactured by Agilent Technologies) under FID conditions. Alternatively, it can be determined as a content of mass with a mass number of m/z 283.8 by the absolute calibration curve method with a gas chromatography mass spectrometer (product name: Agilent 7890A GC/5975C MSD, manufactured by Agilent Technologies) using a capillary column (product name: Rxi-5SiLMS, column length of 30 m, column diameter of 0.25 mm ID, and film thickness of 0.25 μm, manufactured by Restek Corporation).

Moreover, the content of pentachlorobenzene contained in the crystalline material of the compound represented by formula (I) after step (b) can be determined by the absolute calibration curve method with a gas chromatography apparatus (product name: Agilent 7890A, manufactured by Agilent Technologies) using a capillary column (product name: HP-5, column length of 30 m, column diameter of 0.53 mm ID, film thickness of 1.0 μm, manufactured by Agilent Technologies) under FID conditions.

(Step (a'))

The process for producing the compound represented by formula (I) of the present invention may further comprise before the aforementioned step (a), the step of (a') heating the compound represented by the above formula (III) to 100 to 180° C. in the presence of an acid to obtain the compound represented by the above formula (II).

The compound (2,3,5,6-tetrachloro-1,4-benzenedicarbonitrile) represented by formula (III) used in step (a') can be produced by a publicly known production process. For example, it can be produced industrially by reacting 1,4-benzenedicarbonitrile with chlorine.

The acid used in step (a') is not particularly limited, but is preferably sulfuric acid, fuming sulfuric acid, chlorosulfonic acid, or a mixture thereof, and from the viewpoints of the ease of handling, the availability, and the cost, sulfuric acid, in particular 98% sulfuric acid, is preferred among them.

The amount of the acid used in step (a') is preferably 2.0 to 10.0 times by weight, more preferably 3.0 to 8.0 times, and most preferably 4.0 to 6.0 times, relative to the compound represented by formula (III).

The reaction temperature in step (a') is 100 to 180° C., preferably 140 to 170° C., and more preferably 155 to 165° C.

The reaction time in step (a') is not particularly limited, but is preferably 4 to 18 hours, more preferably 5 to 12 hours, and most preferably 6 to 9 hours.

As described above, the process for producing 2,3,5,6-tetrachloroterephthalic acid described in PTL 7 is dangerous in handling a raw material because fuming sulfuric acid is used. By contrast, in step (a') of the present invention, the reaction can proceed by adopting simpler and milder conditions instead of using fuming sulfuric acid.

Water can be added to the reaction mixture containing the compound represented by formula (II) after step (a'). By adding water in this way, the hydrolysis reaction proceeds sufficiently, and finally, a compound represented by formula (I) having a high yield and purity can be obtained. The method for adding water is not particularly limited, but is preferably a method for adding water as a sulfuric acid aqueous solution. The sulfuric acid aqueous solution to be added is not particularly limited, but a 60 to 70% by weight sulfuric acid aqueous solution is preferred from the viewpoint of rendering the conditions simpler and milder than those in the case of using water.

By adding heated water at 30 to 50° C. to the reaction mixture containing the compound represented by formula (II) after the step (a') and then by cooling, the crystalline material of the compound represented by formula (II) can be precipitated. The crystalline material that has been precipitated in this way can be collected by filtration.

By performing centrifugation processing for the reaction mixture after step (a'), containing the compound represented by formula (II), the compound represented by formula (II) can be obtained by the separation.

The compound represented by formula (II) obtained in step (a') can be washed with water. Washing with water can be performed by using a centrifuge. When washing it with water, purification and/or drying processing may be performed, but washing with water may be singly performed without purification and/or drying processing. Here, purification can be carried out by recrystallization with an organic solvent, and drying can be performed under conditions of heating and depressurization by using, for example, a conical drying apparatus, etc. The compound represented by formula (II) after having singly washed with water without performing the purification and/or drying processing as described above, can be used as it is in the next step (a).

The water content of the compound represented by formula (II) after step (a') when used in the next step (a) is preferably 0 to 15% by weight, more preferably 1 to 10% by weight, and most preferably 2 to 6% by weight.

(Composition containing compound represented by formula (I))

One aspect of the present invention is a composition containing the compound represented by formula (I), wherein a content of hexachlorobenzene contained in the composition is more than 0 ppm and 40 ppm or less, and a content of pentachlorobenzene in the composition is more than 0 ppm and 1000 ppm or less.

The content of hexachlorobenzene contained in the composition containing the compound represented by formula (I) is more than 0 ppm and 40 ppm or less, and it may be 0.1 ppm or more and 30 ppm or less, 0.2 ppm or more and 20 ppm or less, or 0.5 ppm or more and 10 ppm or less.

The content of pentachlorobenzene contained in the composition containing the compound represented by formula (I) is more than 0 ppm and 1000 ppm or less, and it may be 1 ppm or more and 500 ppm or less, 5 ppm or more and 250 ppm or less, or 10 ppm or more and 150 ppm or less.

The content of hexachlorobenzene contained in the composition containing the compound represented by formula (I) can be determined by the absolute calibration curve method with a gas chromatography apparatus (product name: Agilent 7890A, manufactured by Agilent Technologies) using a capillary column (product name: HP-5, column length of 30 m, column diameter of 0.53 mm ID, film thickness of 1.0 μm, manufactured by Agilent Technologies) under FID conditions. Alternatively, it can be determined as a content of mass with a mass number of m/z 283.8 by the absolute calibration curve method with a gas chromatography mass spectrometer (product name: Agilent 7890A GC/5975C MSD, manufactured by Agilent Technologies) using a capillary column (product name: Rxi-5SiLMS, column length of 30 m, column diameter of 0.25 mm ID, and film thickness of 0.25 μm, manufactured by Restek Corporation).

The content of pentachlorobenzene contained in the composition containing the compound represented by formula (I) is determined by the absolute calibration curve method with a gas chromatography apparatus (product name: Agilent 7890A, manufactured by Agilent Technologies) using a capillary column (product name: HP-5, a column length of 30 m, a column diameter of 0.53 mm ID, a film thickness of 1.0 μm, manufactured by Agilent Technologies) under FID conditions.

The application of the composition containing the compound represented by formula (I) is not particularly limited, but can be used as a herbicide or a raw material for a herbicide.

The state of the compound represented by formula (I) is not particularly limited, but is preferably in a state of a crystalline material.

The content of the compound represented by formula (I) relative to the entire composition is not particularly limited, but it may be 96.0 to 100% by weight, 97.0 to 99.9% by weight, or 98.0 to 99.9% by weight.

EXAMPLES

Next, Examples of the present invention will be illustrated, but they are given only for explanatory purposes, and the scope of the present invention is in no way limited by the following description since the scope of the present invention is to be determined by the claims.

Example 1, Comparative Examples 1 to 3

[Example 1] Production of Dimethyl 2,3,5,6-tetrachloro-1,4-benzenedicarboxylate (Compound Represented by Formula (I)) from 2,3,5,6-Tetrachloro-1,4-benzenedicarbonitrile (Compound Represented by Formula (III))

(Step 1)

Sulfuric acid (98% by weight, 6348 g) manufactured by Nippon Phosphoric Acid Co., Ltd., was heated to 75° C. in a glass-lined reactor. 2,3,5,6-Tetrachloro-1,4-benzenedicarbonitrile (purity of 98.5% by weight, 1380 g) manufactured by SDS Biotech K.K., was gradually charged to the reactor, and during that period the sulfuric acid solution was maintained at 85 to 100° C. After charging, the reaction mixture was stirred at 100 to 120° C. for 30 minutes. Subsequently, it was heated to 155 to 163° C. and further stirred for another 4 hours. Then, a sulfuric acid aqueous solution (62% by weight, 70 g) was added dropwise to the reaction mixture at 155 to 163° C. and stirred for 2 hours, and a sulfuric acid aqueous solution (62% by weight, 70 g) was further added dropwise at 155 to 163° C. and stirred for 1 hour. Finally, a sulfuric acid aqueous solution (62% by weight, 255 g) was added dropwise to the reaction mixture at 155 to 163° C., and it was stirred for 1 hour. Subsequently, the reaction mixture was cooled to 70 to 80° C., and water (3170 ml) was charged while maintaining the liquid temperature of the reaction mixture below 110° C. After charging, the temperature of the reaction mixture was cooled to 35 to 45° C., and the precipitated solid was collected by filtration. The obtained solid (1611 g) was washed with water (2600 ml). The solid thus obtained was a crystalline material of 2,3,5,6-tetrachloro-1,4-benzenedicarboxylic acid (1609 g) and had a water content of 4% by weight. The crystalline material was used as it was in the next step 2.

(Step 2)
Acetone (2033 ml) and water (300 ml) were charged to a glass-lined reactor so that the water content of acetone was 15% by weight, and then the 2,3,5,6-tetrachloro-1,4-benzenedicarboxylic acid (1609 g) obtained in step 1 and sodium carbonate (754 g) manufactured by Tokyo Chemical Industry Co., Ltd., were charged. The reaction mixture was heated to 57° C. and dimethyl sulfate (1510 g) manufactured by Tokyo Chemical Industry Co., Ltd., was added dropwise while maintaining the liquid temperature of the reaction mixture in the range of 55 to 58° C. Then, the reaction mixture was stirred with heating under reflux for 4.5 hours, and then acetone (1400 ml) was distilled off at normal pressure. Subsequently, heated water (2550 ml) at 40° C. was added to the reaction mixture at a temperature of 50 to 63° C., and the precipitated solid was collected by filtration. The obtained crystalline material (1777 g) was washed with heated water (2550 ml) at 80 to 90° C., and further washed with methanol (1500 ml) at 40° C. Incidentally, the temperature of the crystalline material after washing with heated water and before washing with methanol was 69° C. The crystalline material washed with methanol was collected by Nutsche filtration, and the collected crystalline material was dried under reduced pressure at 80° C. and 40 mmHg to obtain dimethyl 2,3,5,6-tetrachloro-1,4-benzenedicarboxylate.

The obtained dimethyl 2,3,5,6-tetrachloro-1,4-benzenedicarboxylate had a yield amount of 1615 g, a total yield of 93.7% by weight, and a purity of 99.6% by weight, and a content of hexachlorobenzene that was a by-product poisonous to the environment was 1.0 ppm, and a content of pentachlorobenzene was 40 ppm.

Incidentally, in the present Examples, the purity of the desired product was determined by an internal standard method with a gas chromatography apparatus (product name: Agilent 7890A, manufactured by Agilent Technologies) using a capillary column (product name: HP-5, column length of 30 m, column diameter of 0.53 mm ID, and film thickness of 1.0 μm, manufactured by Agilent Technologies) under FID conditions. Moreover, the content of pentachlorobenzene was determined by the absolute calibration curve method with the same gas chromatography apparatus and capillary column under FID conditions as in the case of determination of the purity described above. The content of hexachlorobenzene was determined as a content of mass with a mass number of m/z 283.8 by the absolute calibration curve method with a gas chromatography mass spectrometer (product name: Agilent 7890A GC/5975C MSD, manufactured by Agilent Technologies) using a capillary column (product name: Rxi-5SiLMS, column length of 30 m, column diameter of 0.25 mm ID, film thickness of 0.25 μm, manufactured by Restek Co., Ltd). The quantification limits of the content of hexachlorobenzene and the content of pentachlorobenzene by the measurement method are 0.2 ppm for hexachlorobenzene and 20 ppm for pentachlorobenzene.

[Comparative Example 1] Production of Dimethyl 2,3,5,6-tetrachloro-1,4-benzenedicarboxylate from 2,3,5,6-Tetrachloro-1,4-benzenecarboxamide (Step 1)
The production process of this step 1 is a production process based on the aforementioned PTL 7. In a glass reactor, 2,3,5,6-tetrachloro-1,4-benzenedicarboxamide (6.04 g, 0.02 mol) manufactured by SDS Biotech K.K., and a mixture (in total 17.65 g) of sulfuric acid (96.3% by weight, 12.43 g, containing 0.0256 mol of water) manufactured by Wako Pure Chemical Industries, Ltd., and fuming sulfuric acid (26% by weight, 5.22 g, containing 0.017 mol of $SO_3$) manufactured by Wako Pure Chemical Industries, Ltd., were charged. The reaction mixture was heated to 180° C. under normal pressure and stirred for 6 hours. After completion of the reaction, the precipitated solid was collected by filtration, and the obtained solid (7.0 g) was washed with water (100 ml). The solid obtained by washing with water was dried to obtain a white crystalline material of 2,3,5,6-tetrachloro-1,4-benzenedicarboxylic acid (5.8 g). The obtained crystalline material was used as it was in the next step 2.

(Step 2)
The white crystalline material (5.8 g) of the compound obtained in step 1 was suspended in methanol (17 ml), and a solution of sodium hydroxide (1.43 g) in methanol (12 ml) was added dropwise to the reaction mixture at room temperature over 7 minutes. Then, the mixture was stirred while heating under reflux for 2 hours. After completion of the reaction, the mixture was cooled to room temperature, and the precipitated solid was collected by filtration. The obtained solid was thoroughly washed with water at room temperature (20° C.), the washed solid was collected by filtration, and the collected solid was dried under reduced pressure at 80° C. and 40 mmHg to obtain dimethyl 2,3,5,6-tetrachloro-1,4-benzenedicarboxylate (5.2 g).

The obtained dimethyl 2,3,5,6-tetrachloro-1,4-benzenedicarboxylate had a purity of 99.1% by weight, a hexachlorobenzene content of 25 ppm, and a pentachlorobenzene content of 500 ppm.

[Comparative Example 2] Production of Dimethyl 2,3,5,6-tetrachloro-1,4-benzenedicarboxylate from 2,3,5,6-Tetrachloro-1,4-benzenedicarbonitrile (Step 1)
The production process of this step (1) is a production process based on the aforementioned PTL 7. To a glass reactor, 2,3,5,6-tetrachloro-1,4-benzenedicarbonitrile (purity 98.5% by weight, 5.32 g, 0.02 mol) manufactured by SDS Biotech K.K., and a mixture (in total 17.65 g) of sulfuric acid (90% by weight, 11.06 g) manufactured by Wako Pure Chemical Industries, Ltd. and fuming sulfuric acid (26% by weight, 6.59 g) manufactured by Wako Pure Chemical Industries, Ltd., were charged. The mixture was heated to 160° C. under normal pressure and stirred for 3 hours. After completion of the reaction, the precipitated solid was collected by filtration, and the obtained solid (7.1 g) was washed with water (100 ml). The solid obtained by washing with water was dried to obtain a crystalline material of 2,3,5,6-tetrachloro-1,4-benzenedicarboxylic acid (5.9 g).

(Step 2)

The compound obtained in step 1 was dimethyl esterified by the method described in NPL 1 as follows.

A mixture of a crystalline material of 2,3,5,6-tetrachloro-1,4-benzenedicarboxylic acid (5.9 g) obtained in step 1, acetone (30.3 g), dimethyl sulfate (4.89 g) manufactured by Tokyo Chemical Industry Co., Ltd., and sodium carbonate (2.67 g) manufactured by Tokyo Chemical Industry Co., Ltd., was stirred with heating under reflux for 8 hours. After completion of the reaction, the reaction mixture was cooled to room temperature, water (30 g) was added, and the precipitated solid was collected by filtration. The obtained solid (7.1 g) was washed with 100 g of water at room temperature (20° C.). The solid after washing was a mixture (5.9 g) of dimethyl 2,3,5,6-tetrachloro-1,4-benzenedicarboxylate, methyl 2,3,5,6-tetrachloro-1,4-benzenedicarboxylate, and unreacted 2,3,5,6-tetrachloro-1,4-benzenedicarboxylic acid. The obtained mixture had a hexachlorobenzene content of 21 ppm and a pentachlorobenzene content of 400 ppm.

[Comparative Example 3] Production of Dimethyl 2,3,5,6-tetrachloro-1,4-benzenedicarboxylate from 2,3,5,6-Tetrachloro-1,4-benzenedicarbonitrile (COMPOUND Represented by Formula (III))

Dimethyl 2,3,5,6-tetrachloro-1,4-benzenedicarboxylate was obtained in the same manner as in Step 1 and Step 2 of Example 1, except that for washing of the crystalline material after filtration in Step 2 of Example 1, water at room temperature (20° C.) (2550 ml) and methanol at 20° C. (1500 ml) were used instead of using heated water at 80 to 90° C. (2550 ml) and methanol at 40° C. (1500 ml). Incidentally, the temperature of the crystalline material after washing with water at room temperature (20° C.) and before washing with methanol was 22° C. The obtained compound represented by formula (I) had a hexachlorobenzene content of 10 ppm and a pentachlorobenzene content of 300 ppm.

As demonstrated in Example 1, in the step (Step 1) of industrially producing 2,3,5,6-tetrachloro-1,4-benzenedicarboxylic acid from 2,3,5,6-tetrachloro-1,4-benzenedicarbonitrile that was an industrially produced raw material, the reaction proceeded sufficiently at a reaction temperature of 170° C. or lower by using only commercially available 98% by weight sulfuric acid, and the desired product could be produced in favorable yield. Moreover, in the methyl esterification reaction (step 2) of the next step, the reaction proceeded smoothly by using aqueous acetone, and only the desired dimethyl 2,3,5,6-tetrachloro-1,4-benzenedicarboxylate was obtained efficiently.

Moreover, as a method for washing dimethyl 2,3,5,6-tetrachloro-1,4-benzenedicarboxylate that was the desired product in the final step (step 2) in Example 1, by washing it with heated water at 80 to 90° C. and then further washing with methanol at 40° C., hexachlorobenzene and pentachlorobenzene, etc., which were poisonous to the environment, could be efficiently removed.

On the other hand, in Comparative Example 1, washing of dimethyl 2,3,5,6-tetrachloro-1,4-benzenedicarboxylate that was the desired product in the final step (step 2), was conventionally performed at room temperature (20° C.) only with water, and such a washing method of a crystalline material was found not to enable to sufficiently remove hexachlorobenzene, pentachlorobenzene, etc., which were poisonous to the environment.

Moreover, also in Comparative Example 2, when anhydrous acetone was used in the methyl esterification reaction in step 2, the reaction was stopped in the middle, which resulted in giving a mixture of the unreacted product, the monomethyl ester compound, and the desired product of dimethyl 2,3,5,6-tetrachloro-1,4-benzenedicarboxylate, and the desired product of dimethyl 2,3,5,6-tetrachloro-1,4-benzenedicarboxylate could not be sufficiently obtained.

In Comparative Example 3 in which only the conditions for washing the crystalline material in the final step (step 2) were different from those in Example 1, hexachlorobenzene, pentachlorobenzene, etc., which were poisonous to the environment, could not be sufficiently removed since as a method for washing dimethyl 2,3,5,6-tetrachloro-1,4-benzenedicarboxylate that was the desired product in the final step, it was washed with water at room temperature (20° C.) and methanol at 20° C., which were lower in temperature than in Example 1.

Therefore, it was found that by converting 2,3,5,6-tetrachloro-1,4-benzenedicarbonitrile to 2,3,5,6-tetrachloro-1,4-benzenedicarboxylic acid with commercially available 98% by weight sulfuric acid, by using aqueous acetone as a solvent in the methyl esterification reaction of the next step, and by washing the desired product, dimethyl 2,3,5,6-tetrachloro-1,4-benzenedicarboxylate with heated water at 30 to 100° C. and then further washing it with an organic solvent at 30 to 80° C., a desired product having high purity and a reduced content of impurities poisonous to the environment could be industrially produced.

Examples 2 to 10, Comparative Examples 4 to 8

Examination of Washing Conditions in Production of Dimethyl 2,3,5,6-tetrachloro-1,4-benzenedicarboxylate from 2,3,5,6-Tetrachloro-1,4-benzenedicarbonitrile As raw materials, sulfuric acid and 2,3,5,6-tetrachloro-1,4-benzenedicarbonitrile that were similar to those in step 1 of Example 1, were used, and the production was carried out by the same process and conditions as in step 1 of Example 1, and then, a crystalline material of 2,3,5,6-tetrachloro-1,4-benzenedicarboxylic acid (1600 g) having a water content of 4% by weight was isolated. The obtained crystalline material was divided into 200 g portions, giving each of lots 1 to 8, respectively. Each lot is used as it is in the next step.

Further, a crystalline material of 2,3,5,6-tetrachloro-1,4-benzenedicarboxylic acid (1200 g) having a water content of 4% by weight was prepared by the same method as described above. The obtained crystalline material was divided into 200 g portions, giving lots 9 to 14, respectively. Each lot is used as it is in the next step.

Example 2

To a glass-lined reactor, acetone (254 ml) and water (37 ml) were charged so that the water content of acetone was 15% by weight, then 2,3,5,6-tetrachloro-1,4-benzenedicarboxylic acid (lot 1, 200 g) and sodium carbonate (94 g) manufactured by Tokyo Chemical Industry Co., Ltd., were charged, the temperature of the reaction mixture was raised to 57° C., and dimethyl sulfate (189 g) manufactured by Tokyo Chemical Industry Co., Ltd., was added dropwise to the reaction mixture at the temperature of 55 to 58° C. After the dropping, the mixture was stirred with heating under reflux for 4.5 hours. Then, acetone (175 ml) was distilled off under normal pressure. Subsequently, water (320 ml) at 20° C. was added to the reaction mixture at a temperature of 50 to 53° C., and the precipitated solid was collected by filtration. The obtained crystalline material (221 g) was washed with heated water (320 ml) at 85 to 90° C., and further washed with methanol (188 ml) at 40° C. The temperature of the crystalline material after washing with heated water and before washing with methanol was 72° C. The obtained crystalline material was collected by Nutsche filtration, the collected crystalline material was dried under reduced pressure at 80° C. and 40 mmHg to obtain dimethyl 2,3,5,6-tetrachloro-1,4-benzenedicarboxylate. The obtained dimethyl 2,3,5,6-tetrachloro-1,4-benzenedicarboxylate had a yield amount of 201.7 g, a purity of 98.749% by weight, a hexachlorobenzene content of 0.8 ppm and a pentachlorobenzene content of 30 ppm that were by-products poisonous to the environment.

Example 3

To a glass-lined reactor, acetone (1015 ml) and water (172 ml) were charged so that the water content of acetone was 15% by weight, then 2,3,5,6-tetrachloro-1,4-benzenedicarboxylic acid (lot 2, 200 g) and sodium carbonate (94 g) manufactured by Tokyo Chemical Industry Co., Ltd. were charged, the temperature of the reaction mixture was raised to 57° C., and dimethyl sulfate (189 g) manufactured by Tokyo Chemical Industry Co., Ltd., was added dropwise to the reaction mixture at the temperature of 55 to 58° C. After the dropping, the mixture was stirred with heating under reflux for 4.5 hours. Then, acetone (175 ml) was distilled off at normal pressure. Subsequently, water (320 ml) at 20° C. was added to the reaction mixture at a temperature of 50 to 53° C., and the precipitated solid was collected by filtration. The obtained crystalline material was washed with heated water (160 ml) at 85 to 90° C. or higher, and further washed with methanol (188 ml) at 40° C. The temperature of the crystalline material after washing with heated water and before washing with methanol was 59° C. The obtained crystalline material was collected by Nutsche filtration, and the collected crystalline material was dried under reduced pressure at 80° C. and 40 mmHg to obtain dimethyl 2,3,5,6-tetrachloro-1,4-benzenedicarboxylate. The obtained dimethyl 2,3,5,6-tetrachloro-1,4-benzenedicarboxylate had a yield amount of 201.9 g, a purity of 98.241% by weight, a hexachlorobenzene content of 8.1 ppm and a pentachlorobenzene content of 30 ppm that were by-products poisonous to the environment. The temperatures and amounts of the washing water and methanol used, the temperature of the crystalline material after washing with heated water and before washing with methanol, the yield and the purity of dimethyl 2,3,5,6-tetrachloro-1,4-benzenedicarboxylate, and the contents of by-products poisonous to the environment are shown in Table 1 below.

TABLE 1

|  | Example 2 Lot 1 | Example 3 Lot 2 | Example 4 Lot 3 | Example 5 Lot 4 | Example 6 Lot 5 | Comparative Example 4 Lot 6 | Comparative Example 5 Lot 7 | Comparative Example 6 Lot 8 |
| --- | --- | --- | --- | --- | --- | --- | --- | --- |
| Washing water temperature | ≥85° C. | ≥85° C. | ≥85° C. | 45° C. | 65° C. | 20° C. | 20° C. | 20° C. |
| Washing water amount | 320 ml | 16 ml | 160 ml | 320 ml | 320 ml | 320 ml | 320 ml | 320 ml |
| Organic solvent used | Methanol | Methanol | Methanol | Methanol | Methanol | — | Methanol | Methanol |
| Organic solvent temperature | 40° C. | 40° C. | 40° C. | 40° C. | 40° C. | — | 40° C. | 40° C. |
| Washing amount of organic solvent | 188 ml | 188 ml | 94 ml | 188 ml | 188 ml | — | 188 ml | 188 ml |
| Temperature of crystalline material before organic solvent washing | 72° C. | 59° C. | 61° C. | 40° C. | 49° C. | 24° C. | 29° C. | 25° C. |
| Yield amount | 201.7 g | 201.9 g | 202.2 g | 202.5 g | 202.6 g | 203.9 g | 203.0 g | 203.2 g |
| Purity (% by weight) | 98.749% | 98.241% | 98.223% | 98.055% | 98.077% | 97.558% | 97.581% | 97.554% |
| Hexachlorobenzene concentration | 0.8 ppm | 8.1 ppm | 9.4 ppm | 29.2 ppm | 15.2 ppm | 35.4 ppm | 34.3 ppm | 35.3 ppm |
| Pentachlorobenzene concentration | 30 ppm | 30 ppm | 30 ppm | 280 ppm | 150 ppm | 360 ppm | 280 ppm | 340 ppm |

TABLE 2

|  | Example 7 Lot 9 | Example 8 Lot 10 | Example 9 Lot 11 | Example 10 Lot 12 | Comparative Example 7 Lot 13 | Comparative Example 8 Lot 14 |
| --- | --- | --- | --- | --- | --- | --- |
| Washing water temperature | ≥85° C. | ≥85° C. | 45° C. | 45° C. | 20° C. | 20° C. |
| Washing water amount | 320 ml | 320 ml | 320 ml | 320 ml | 320 ml | 320 ml |
| Organic solvent used | Ethanol | Isopropanol | Ethanol | Isopropanol | Ethanol | Isopropanol |
| Organic solvent temperature | 40° C. | 40° C. | 40° C. | 40° C. | 40° C. | 40° C. |
| Washing amount of organic solvent | 188 ml | 188 ml | 188 ml | 188 ml | 188 ml | 188 ml |
| Temperature of crystalline material before organic solvent washing | 74° C. | 73° C. | 38° C. | 38° C. | 18° C. | 18° C. |
| Yield amount | 202.0 g | 202.4 g | 203.1 g | 203.5 g | 203.3 g | 203.27 g |
| Purity (% by weight) | 98.581% | 98.104% | 98.005% | 97.899% | 97.508% | 97.391% |
| Hexachlorobenzene concentration | 2.4 ppm | 3.1 ppm | 29.0 ppm | 29.1 ppm | 35.8 ppm | 35.5 ppm |
| Pentachlorobenzene concentration | 30 ppm | 30 ppm | 260 ppm | 280 ppm | 350 ppm | 380 ppm |

Examples 4 to 10, Comparative Examples 4 to 8

Dimethyl 2,3,5,6-tetrachloro-1,4-benzenedicarboxylate of each of Examples 4 to 6 and Comparative Examples 4 to 6 was obtained in the same manner as in Example 3, except that the temperatures and amounts of washing water and methanol used were changed as shown in Table 1. With respect to the obtained dimethyl 2,3,5,6-tetrachloro-1,4-benzenedicarboxylate, the yield, the purity, the contents of hexachlorobenzene and pentachlorobenzene that are by-products poisonous to the environment, and the temperature of the crystalline material after washing with heated water and before washing with methanol, are shown in Table 1, respectively.

Moreover, dimethyl 2,3,5,6-tetrachloro-1,4-benzenedicarboxylate each of Examples 7 to 10 and Comparative Examples 7 and 8 was obtained in the same manner as in Example 3, except that the temperatures and amounts of the washing water and the organic solvent used and the type of organic solvents were changed as shown in Table 2. With respect to the obtained dimethyl 2,3,5,6-tetrachloro-1,4-benzenedicarboxylate, the yield, the purity, the contents of hexachlorobenzene and pentachlorobenzene that are by-products poisonous to the environment, and the temperature of the crystalline material after washing with heated water and before washing with the organic solvent, are shown in Table 2, respectively.

As can be seen from the results in Table 1, it was found that in Examples 2 to 10 in which the crystalline material was washed with heated water at 30 to 100° C. and then further washed with an organic solvent at 30 to 80° C., the contents of hexachlorobenzene and pentachlorobenzene in the crystalline material after the washing were low, and they were sufficiently removed. Moreover, it was found that in Examples 2 to 4, 7, and 8 in which the crystalline material was washed with heated water at 85° C. or higher, the contents of hexachlorobenzene and pentachlorobenzene in the crystalline material were further reduced, and these by-products were efficiently removed. It is presumed that in Examples 2 to 10 each, the temperature of the crystalline material after having washed with heated water and before washing with an organic solvent is relatively high, whereby the aforementioned by-products can be sufficiently removed.

By contrast, it was found that in Comparative Example 4 in which the crystalline material was washed only with water at 20° C., in Comparative Example 5 in which the crystalline material was washed with water at 20° C. and then further washed with an organic solvent at 30 to 80° C., and in Comparative Examples 6 to 8 in which the crystalline material was washed with water at 20° C. and then washed with an organic solvent at 20° C., the contents of hexachlorobenzene and pentachlorobenzene in the crystalline material after the washing were high and were not sufficiently removed.

INDUSTRIAL APPLICABILITY

The present invention provides, when producing dimethyl 2,3,5,6-tetrachloro-1,4-benzenedicarboxylate useful as agricultural or horticultural herbicides, an industrial process capable of reducing the content of by-product poisonous to the environment, such as hexachlorobenzene and pentachlorobenzene, compared with that by the conventional process to thereby enable the efficient production of dimethyl 2,3,5,6-tetrachloro-1,4-benzenedicarboxylate. Accordingly, the present invention has industrial applicability.

The invention claimed is:

1. A process for producing a compound represented by formula (I):

[Chemical Formula 1]

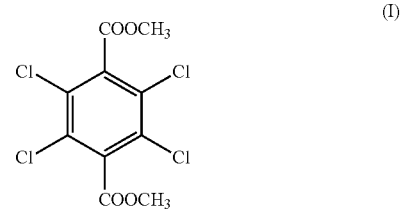

the process comprising the steps of
(a) reacting a compound represented by formula (II):

[Chemical Formula 2]

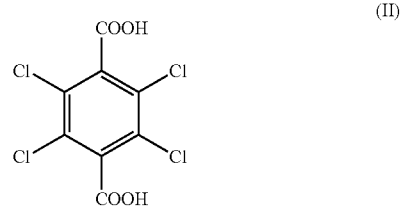

with dimethyl sulfate in the presence of an alkali carbonate in a aqueous ketone solvent to obtain the compound represented by formula (I) as a crystalline material, and
(b) washing the crystalline material with heated water at 30 to 100° C. and then further washing the crystalline material with an organic solvent at 30 to 80° C.

2. The process according to claim 1, wherein step (b) is a step of reducing the content of a poisonous by-product contained in the crystalline material by washing the crystalline material with an organic solvent under heating.

3. The process according to claim 1, wherein in step (b), a temperature of the crystalline material after washing with heated water and before washing with an organic solvent is 40 to 90° C.

4. The process according to claim 1, wherein a temperature of the heated water is 60 to 95° C.

5. The process according to claim 1, wherein the organic solvent in step (b) is an alcohol.

6. The process according to claim 1, wherein the organic solvent in step (b) is methanol, ethanol, isopropanol, or a mixture thereof.

7. The process according to claim 1, wherein the organic solvent in step (b) is methanol.

8. The process according to claim 5, wherein a temperature of the organic solvent is 35 to 65° C.

9. The process according to claim 1, further comprising, before step (a), the step of (a') heating a compound represented by formula (III):

[Chemical Formula 3]

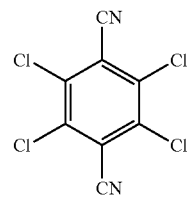

to 100 to 180° C. in the presence of an acid to obtain the compound represented by formula (II).

10. The process according to claim 9, wherein the compound represented by formula (II) obtained in step (a') is used in step (a) after being washed with water.

11. The process according to claim 1, wherein the aqueous ketone solvent in step (a) is aqueous acetone.

12. The process according to claim 1, wherein a water content of the aqueous ketone solvent in step (a) is 5 to 25% by weight.

13. The process according to claim 1, wherein the alkali carbonate in step (a) is sodium carbonate.

14. The process according to claim 2, wherein the poisonous by-product is polychlorobenzenes.

15. The process according to claim 14, wherein the polychlorobenzenes are hexachlorobenzene, pentachlorobenzene, or a mixture thereof.

16. The process according to claim 2, wherein the organic solvent in step (b) is an alcohol.

17. The process according to claim 3, wherein the organic solvent in step (b) is an alcohol.

18. The process according to claim 2, wherein the organic solvent in step (b) is methanol, ethanol, isopropanol, or a mixture thereof.

19. The process according to claim 3, wherein the organic solvent in step (b) is methanol, ethanol, isopropanol, or a mixture thereof.

20. The process according to claim 2, further comprising, before step (a), the step of (a') heating a compound represented by formula (III):

[Chemical Formula 3]

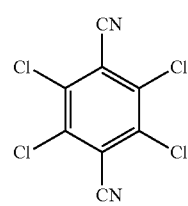

to 100 to 180° C. in the presence of an acid to obtain the compound represented by formula (II).

21. The process according to claim 3, further comprising, before step (a), the step of (a') heating a compound represented by formula (III):

[Chemical Formula 3]

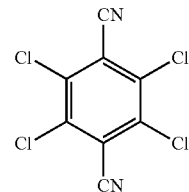

to 100 to 180° C. in the presence of an acid to obtain the compound represented by formula (II).

22. The process according to claim 5, further comprising, before step (a), the step of (a') heating a compound represented by formula (III):

[Chemical Formula 3]

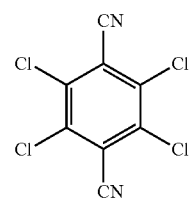

to 100 to 180° C. in the presence of an acid to obtain the compound represented by formula (II).

23. The process according to claim 16, further comprising, before step (a), the step of (a') heating a compound represented by formula (III):

[Chemical Formula 3]

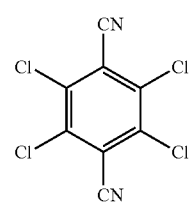

to 100 to 180° C. in the presence of an acid to obtain the compound represented by formula (II).

24. The process according to claim 6, further comprising, before step (a), the step of (a') heating a compound represented by formula (III):

[Chemical Formula 3]

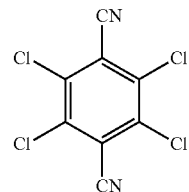
(III)

to 100 to 180° C. in the presence of an acid to obtain the compound represented by formula (II).

25. The process according to claim 18, further comprising, before step (a), the step of (a') heating a compound represented by formula (III):

[Chemical Formula 3]

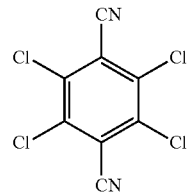
(III)

to 100 to 180° C. in the presence of an acid to obtain the compound represented by formula (II).

* * * * *